US012703115B2

(12) United States Patent
Li et al.

(10) Patent No.: US 12,703,115 B2
(45) Date of Patent: Aug. 11, 2026

(54) DETACHABLE MANIPULATOR AND SURGICAL ROBOT COMPRISING SAME

(71) Applicant: Chengdu Borns Medical Robotics Inc., Sichuan (CN)

(72) Inventors: Yao Li, Sichuan (CN); Zhiqiang Li, Sichuan (CN)

(73) Assignee: Chengdu Borns Medical Robotics Inc., Chengdu (CN)

( * ) Notice: Subject to any disclaimer, the term of this patent is extended or adjusted under 35 U.S.C. 154(b) by 354 days.

(21) Appl. No.: 18/561,686

(22) PCT Filed: May 17, 2022

(86) PCT No.: PCT/CN2022/093317
§ 371 (c)(1),
(2) Date: Nov. 16, 2023

(87) PCT Pub. No.: WO2022/242638
PCT Pub. Date: Nov. 24, 2022

(65) Prior Publication Data

US 2024/0238993 A1 Jul. 18, 2024

(30) Foreign Application Priority Data

May 19, 2021 (CN) ......................... 202110547391.9
Jun. 16, 2021 (CN) ......................... 202110663277.2
Jun. 16, 2021 (CN) ......................... 202110667672.8

(51) Int. Cl.
*B25J 18/02* (2006.01)
*A61B 34/30* (2016.01)

(52) U.S. Cl.
CPC ............ *B25J 18/025* (2013.01); *A61B 34/30* (2016.02)

(58) Field of Classification Search
CPC .......... A61B 34/30; B25J 15/04; B25J 18/025
See application file for complete search history.

(56) References Cited

U.S. PATENT DOCUMENTS

2016/0015419 A1* 1/2016 Hibner ............... A61B 18/1482 606/171
2017/0224375 A1 8/2017 Robertson et al.
2017/0281286 A1 10/2017 Braun

FOREIGN PATENT DOCUMENTS

CN 104023652 2/2017
CN 108697477 10/2018

(Continued)

OTHER PUBLICATIONS

PCT International Application for PCT/CN2022/093317 mailed Aug. 26, 2022, 6 pages.

(Continued)

*Primary Examiner* — Scott Luan

(57) ABSTRACT

The invention discloses a quickly detachable manipulator device, which comprises a power seat, an end effector and an instrument rod used for connecting the power seat and the end effector, wherein the instrument rod comprises a rod snap-fitting member and a rod body connected to rod snap-fitting member, a rotary fixing member is provided over the rod body, and a locking ring member is provided over the rod snap-fitting member; the power seat comprises a rotating shaft and a sliding member, the rotary fixing member is detachably connected to the rotating shaft, and the locking ring member is detachably connected to the sliding member. By detachably connecting the locking ring member to the sliding member and the rotary fixing member to the rotating shaft, disassembly and assembly of the instrument rod is realized, the assembly and use of disposable appliances of the end effector are realized, and the effective fitting and fixing of the end effector are ensured. The cost of the equipment is reduced, and the overall operation efficiency is also improved. The operation accuracy and manipulation stability are not affected while the quick disassembly and assembly is realized.

19 Claims, 6 Drawing Sheets

(56) References Cited

FOREIGN PATENT DOCUMENTS

| | | | | |
|---|---|---|---|---|
| CN | 208362711 | | 1/2019 | |
| CN | 110064945 | | 7/2019 | |
| CN | 209404947 | | 9/2019 | |
| CN | 110613509 A | * | 12/2019 | ............ A61B 34/70 |
| CN | 111012385 | | 4/2020 | |
| CN | 111012389 | | 4/2020 | |
| CN | 110613509 | | 5/2020 | |
| CN | 108175452 | | 9/2020 | |
| CN | 111904511 | | 11/2020 | |
| CN | 211834686 | | 11/2020 | |
| CN | 212779282 | | 3/2021 | |
| CN | 107320156 | | 4/2021 | |
| CN | 107374735 | | 7/2021 | |
| CN | 109068937 | | 7/2021 | |
| CN | 112971995 | | 8/2021 | |
| CN | 113251130 | | 8/2021 | |
| CN | 113334417 | | 6/2022 | |
| CN | 113952034 | | 5/2023 | |
| CN | 113951987 | | 9/2023 | |

OTHER PUBLICATIONS

Chinese First Office Action for CN Application No. 202110547391.9, 5 pages.

Chinese Search Report for CN Application No. 202110547391.9, 2 pages.

Chinese Search Report for CN Application No. 202110663277.2, 1 page.

* cited by examiner

DETACHABLE MANIPULATOR AND SURGICAL ROBOT COMPRISING SAME

TECHNICAL FIELD

The invention relates to technical field of a manipulator, in particular to a detachable manipulator device and a surgical robot including the manipulator device.

BACKGROUND

Manipulator is a mechanical tool used for grasping. For the existing manipulator devices, they are often used to carry objects, drive tool to change angles, and fixedly grasp. Therefore, the manipulator devices are widely used in mechanical manufacturing, electronics, light industry, and medical fields.

Surgical robot has developed rapidly in recent years, and a large number of instruments designed for surgical robot have been developed continuously. Most of the end effector devices that will be operated in a human body usually adopt disposable design, which can completely eliminate the risk caused by reuse and significantly reduce the risk of surgical infection.

However, in the current surgical robot, the connection between an instrument rod and a driving device is relatively complex. In order to meet the accuracy requirement, the instrument rod and the driving device are conventionally designed in one piece, which has the advantage of ensuring the precision of the operation of the instrument. However, the overall cost is relatively high. However, traditional detachable surgical instruments cannot meet the accuracy requirements for surgical operation.

SUMMARY OF THE INVENTION

The present disclosure is made in view of the problems in the prior art. Therefore, the present disclosure aims to provide a detachable manipulator device, which comprises a power seat, an instrument rod extending from the power seat, and an end effector arranged at a distal end of the instrument rod, wherein the instrument rod is detachably mounted on the power seat to transmit the rotary motion and sliding motion of the power seat to the end effector.

Therefore, after the operation is completed, the instrument rod and the surgical end effector mounted thereon can be detached from the power seat, and the power seat can continue to mate with another new instrument rod and surgical end effector without being discarded together with the used end effector, thus saving the cost.

In one embodiment, the instrument rod comprises an outer rod and an inner rod, and the inner rod is arranged in the outer rod so as to be axially movable relative to the outer rod and non-rotatable relative to the outer rod.

In one embodiment, the power seat comprises a housing, a rotary driving device and a sliding driving device provided in the housing, wherein the rotary driving device drives the outer rod and the inner rod to rotate, and the sliding driving device drives the inner rod to slide in the axial direction.

In one embodiment, that rotary driving device drives a rotating shaft to rotate, and the out rod is detachably engaged with the rotating shaft to rotate together with the rotating shaft and is axially fixed relative to the rotating shaft.

The connection between the rotating shaft and the outer rod can adopt a shape fit connection with a non-circular cross section. In one embodiment, wherein the outer rod comprises a flat shaft segment with a non-circular cross section, the rotating shaft comprises a central hole with a corresponding non-circular cross section, and the flat shaft segment of the outer rod is inserted into the central hole.

The detachable connection between the instrument rod and the power seat can be realized by threaded connection. In one embodiment, the outer rod is further provided with a positioning flange, and a locking nut is further provided, which is threaded with the distal end of the rotating shaft to sandwich the positioning flange of the outer rod between the locking nut and the rotating shaft, so that the outer rod is axially fixed with the rotating shaft.

In one embodiment, the outer peripheral face of the rotating shaft is further provided with a gear to receive rotational input; the housing is provided with a locking mechanism which is selectively engaged with the gear to prevent the rotation of the rotating shaft.

In one embodiment, the locking mechanism includes a button, a pressing spring tab driven by the button to engage with the gear, and an elastic member that biases the button towards a state where the pressing spring tab is disengaged from the gear.

In one embodiment, the sliding driving device comprises a slider, and the inner rod is threadedly connected with the slider.

In one embodiment, the proximal end of the inner rod is provided with threads, and the slider is provided with threaded fixing shaft which is rotatable but axially fixed relative to the slider, and the screw threads of the inner rod is in threaded engagement with the threaded fixing shaft.

In one embodiment, the slider is further provided with an anti-rotation mechanism that selectively prevents the threaded fixing shaft from rotating.

In one embodiment, the anti-rotation mechanism includes an engagement pressing tab operable from the outside of the housing, the engagement pressing tab includes a feature capable of engaging the outer periphery of the threaded fixing shaft to prevent the threaded fixing shaft from rotating, and can move between a locking position in which the feature engages with the threaded fixing shaft and a disengaged position in which the feature is disengaged from the threaded fixing shaft, and a spring is further provided to bias the engagement pressing tab toward the disengaged position.

In one embodiment, the inner side of the housing is also provided with a stop block, and the stop block prevents the engagement pressing tab from being placed in the locking position in operation range of the slider.

Alternatively, the detachable connection between the instrument rod and the power seat can be realized by snap-fit, etc. In one embodiment, the outer rod of the instrument rod is fixedly connected with a rotary fixing member, the distal end of the rotary fixing member includes an elastically deflectable inverted hook, and the proximal end of the rotary fixing member includes a flange. The rotary fixing member is inserted into the central hole of the rotating shaft, so that the inverted hook is snap-fitted on the distal end face of the rotating shaft, and the flange abuts against the proximal end face of the rotating shaft.

In one embodiment, at least one protruding boss is formed on the end face of the flange of the rotary fixing member facing the proximal end face of the rotating shaft, and at least one groove is formed on the proximal end face of the rotating shaft, and the protruding boss can be fitted into the groove.

In one embodiment, the outer rod is connected with the rotary fixing member by a pin.

In one embodiment, the sliding driving device comprises a slider including a central hole, and the proximal end of the inner rod is provided with a locking ring member, and the locking ring member is detachably fitted in the central hole of the slider.

In one embodiment, the outer peripheral face of the locking ring member includes a snap-fitting groove, and the side wall of the slider is provided with a locking tongue which can move between a locking position engaged in the snap-fitting groove and a disengaged position disengaged from the snap-fitting groove. A spring may also be included, which biases the locking tongue toward the locking position.

In order to actuate the locking tongue, a locking button provided on the side wall of the slider is further included, and the locking button can be actuated from the outside of the housing to drive the locking tongue toward the disengaged position.

In one embodiment, the locking ring member includes a central hole, and the inner rod is rotatably but axially immovably arranged in the central hole of the locking ring member.

In another aspect of the present disclosure, a surgical robot is provided, which includes a rotary driver and a sliding driver, and includes a detachable manipulator device as mentioned above. The housing of the manipulator device includes a rotary driving input joint and a sliding driving input joint, wherein the rotary driving input joint can be connected with the rotary driver, and the sliding driving input joint can be connected with the sliding driver.

In the power seat, an input gear is rotatably arranged in the housing, connected with the rotary driving input joint, and meshed with the gear of the rotating shaft.

In the power seat, a lead screw is rotatably provided in the housing, connected with the sliding driving input joint, and engaged with the slider to drive the slider to slide along the axial direction of the lead screw.

Compared with the prior art, the above-mentioned technical solution has the following advantages:

With the detachable manipulator device provided by the present disclosure, the stable disassembly and assembly of the instrument rod with the power seat is achieved, reliable installation and use of the disposable end effector of the manipulator device in a surgical robot is ensured, the effective fitting and fixation of the instrument rod of the end effector is achieved by detachably connecting the locking ring member to the sliding member and detachably connecting the rotating fixed piece to the rotating shaft, which reduces the cost of equipment, and also improves the overall operation efficiency. In addition to rapid disassembly and assembly, the operation accuracy and manipulation stability can also be ensured.

BRIEF DESCRIPTION OF THE DRAWINGS

Various embodiments are depicted in the accompanying drawings for illustrative purposes and should in no way be interpreted as limiting the scope of the inventions. It can be appreciated by the person skilled in that art that the present disclosure is not limited to the embodiments shown in the accompanying drawings and can be varied or modified to obtain other embodiments under the teaching of the present disclosure.

DETAILED DESCRIPTION OF THE PREFERRED EMBODIMENTS

In order to make the above objects, features, and advantages of the present invention more obvious and easier to understand, the following detailed description will be made of the specific embodiments of the present invention with reference to the accompanying drawings.

In the following description, specific details are set forth in the following description to facilitate a full understanding of the present invention. However, the invention can be implemented in many other ways different from those described here, and those skilled in the art can make similar improvement without departing from the spirit of the disclosure. Therefore, the present invention is not limited by the specific embodiments disclosed below.

In the following description and appended claims, directional terms such as "distal side" and "proximal side" are used. In the case of surgical robot, the distal side refers to the side close to the patient undergoing surgery, while the proximal side is the side opposite to the distal side. In addition, "longitudinal direction", "axial direction" or "longitudinal axis direction" refers to the direction along the longest dimension of the described feature, while "peripheral direction" refers to the direction around longitudinal direction or longitudinal axis direction, and "radial direction" refers to the direction perpendicular to longitudinal direction.

Figure 1:
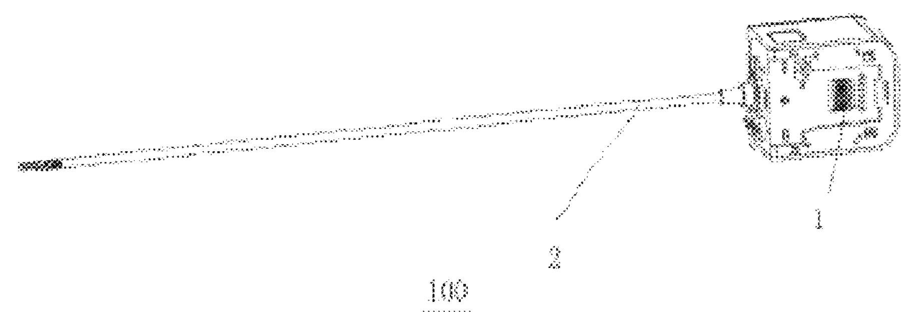
FIG. 1 is a perspective view showing a manipulator.

FIG. 1 is a perspective view showing a manipulator device, which, for example, is connected with a driver (not shown) of a surgical robot and performs surgical operation on a patient under the control of a doctor. As shown in FIG. 1, the manipulator device 100 includes a power seat 1, an instrument rod 2 extended distally from the power seat 1, and an end effector provided at the distal end of the instrument rod 2. The end effector can be any instrument suitable for surgery, such as a scalpel, an electric hook, a clip, a suture forceps, a hemostatic forceps, etc., and can also be an assistance instrument in surgery, such as an endoscope lens, an illuminating lamp, etc., and the present disclosure is not limited thereto.

In the prior art, the manipulator device 100 as a whole can be quickly connected to the driver of the surgical robot, and it will be replaced or discarded as a whole after the operation is finished due to contamination. This leads to waste and increased costs.

In view of the problems existing in the prior art, according to the present disclosure, a detachable manipulator device is provided, in which the instrument rod 2 can be easily mounted on to or detached from the power seat 1, whereby only the instrument rod 2 can be detached and discarded after the surgical operation, and the power seat 1 can be reused, thereby reducing the cost of the whole instrument. The instrument rod 2 can be mounted on the power seat 1 by any detachable connection such as a threaded connection, snap connection, etc., the present disclosure is not limited thereto.

Figure 2:
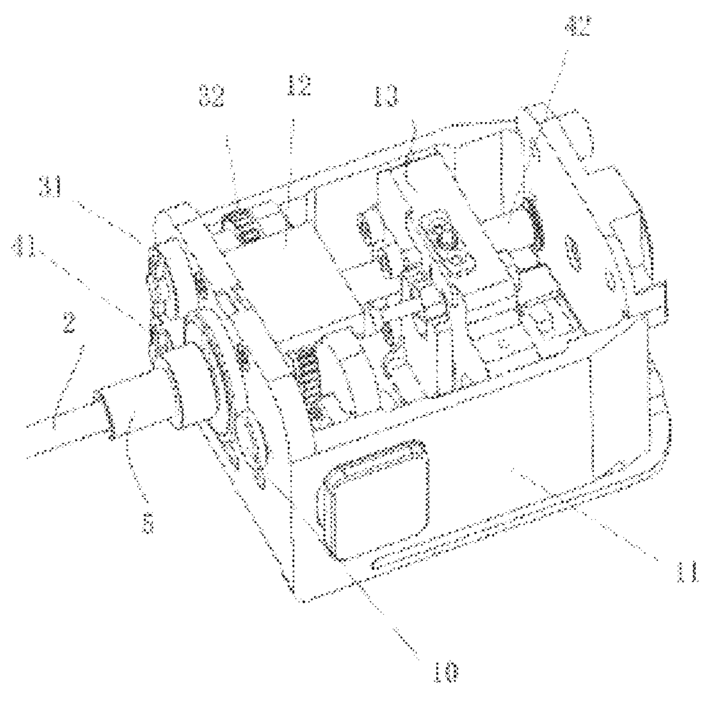
FIG. 2 is a schematic view showing a power seat of the detachable manipulator device according to one embodiment of the present disclosure with the housing being opened to show the internal structure.

The embodiments according to the present disclosure are described in detail below with reference to the accompanying drawings. FIGS. 2 to 7 illustrate a detachable manipulator device according to one embodiment of the present disclosure. As shown in FIG. 2, the detachable manipulator device includes an instrument rod 2 and a power seat 1 for mounting the instrument rod 2. The instrument rod 2 is detachably connected with the power seat 1, so that after surgical operation, only the instrument rod 2 is disposable, and the power device can be reused to reduce the cost of the whole device.

The power seat 1 comprises a housing 11, a rotary driving device 12 and a sliding driving device 13 both provided in the housing, wherein the instrument rod 2 is connected to the rotary driving device 12 and the sliding driving device 13, so that the instrument rod 1 is driven to rotate by the rotary driving device 12 and is driven to move along its axial direction by the sliding driving device 13, thereby driving the end effector (not labeled) arranged at the distal end of the instrument rod 2 to rotate and move as required, or causing the surgical instrument to be opened and closed through the movement of the instrument rod 2. Since the operation of the end effector provided at the end of the instrument rod 2 is not the main aspect of the present disclosure, and it can be designed and constructed by the techniques known in the art, the description thereof will be omitted here.

Figure 3:
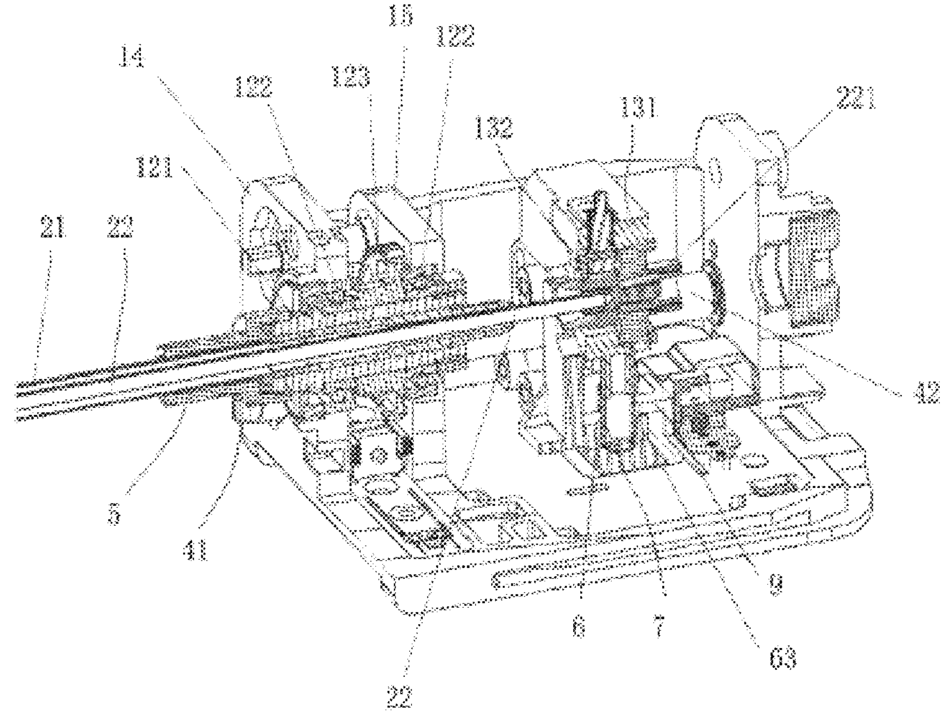
FIG. 3 is a cross-section view showing the power seat of the detachable manipulator device shown in FIG. 2.
Figure 4:
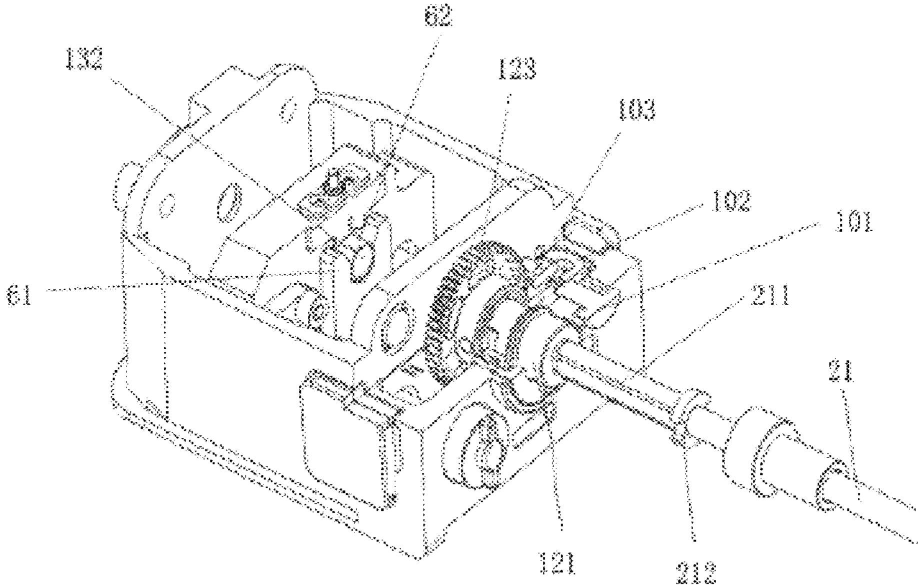
FIG. 4 is another schematic view showing the power seat of the detachable manipulator device shown in FIG. 2.

FIGS. 3 and 4 are cross-section views showing the relevant parts of the power seat 1 and the instrument rod 2. As shown in FIGS. 3 and 4, the instrument rod 2 has a double-layer structure, including an outer rod 21 and an inner rod 22 inside the outer rod 21. The outer rod 21 includes a flat shaft segment 211 on the proximal side and a positioning flange 212 provided at the distal end of the flat shaft segment 211. The inner rod 22 can be slid axially in the outer rod 21 relative to the outer rod 21 but is prevented from rotating, so that the axial movement of the inner rod 22 can, for example, open and close the end effector provided at the distal end of the instrument rod.

The rotary driving device 12 includes a rotating shaft 121 rotatably supported on an end wall 14 and a middle support wall 15 of the housing 11 through bearings 122, by which the rotating shaft 121 can be driven to rotate. A part of the outer periphery of the rotating shaft may be provided with a gear 123, the gear 123 may be integrally formed with the rotating shaft 121 or fixed to the rotating shaft 121 by any known means, such as welding, spline connection, bonding, etc. The gear 123 is engaged with a driving gear 32 (see FIG. 5), which is engaged with a rotary driver (not shown) of the surgical robot through a rotary driving input joint 31 protruding out of the housing 11, thereby driving the gear 123 and further driving the rotating shaft 121 to rotate as required.

The distal end of the rotating shaft 121 includes external threads (not shown), and a central hole is formed in the axial direction. The central hole includes at least a flat sectional segment, and the flat shaft segment 211 of the instrument rod 2 is inserted into the hole and engaged with the flat sectional segment until the positioning flange 212 provided on the outer periphery of the instrument rod 2 abuts against the distal end face of the rotating shaft 121. Thereby, the rotation of the rotating shaft 121 can drive the outer rod 21 of the instrument rod 2 to rotate.

In order to detachably fix the instrument rod 2 to the rotating shaft 121, a locking nut 5 is provided. The locking nut 5 includes an internal thread and is screwed on an external thread (not labeled) at the distal end of the rotating shaft 121, thereby pressing the positioning flange 212 of the instrument rod 2 against the distal end surface of the rotating shaft 121, so that the outer rod 21 of the instrument rod 2 cannot move axially relative to the rotating shaft 121, and by the flat shaft segment 211 of the outer rod 21 of the instrument rod 2 engaged with the flat sectional segment of the center hole 122 of the rotating shaft 121, the rotating shaft 121 can be rotated together with the outer rod 21 of the instrument rod 2.

As mentioned herein, the flat shaft segment or the flat sectional segment means that the section thereof is non-circular, so that the two parts combined with each other can be prevented from rotating relative to each other. However, the present disclosure is not limited to this, but other anti-rotation structure can be used, such as splines, keyways, teeth, arcs including planes, etc., and the present disclosure is not limited to this.

Figure 5:
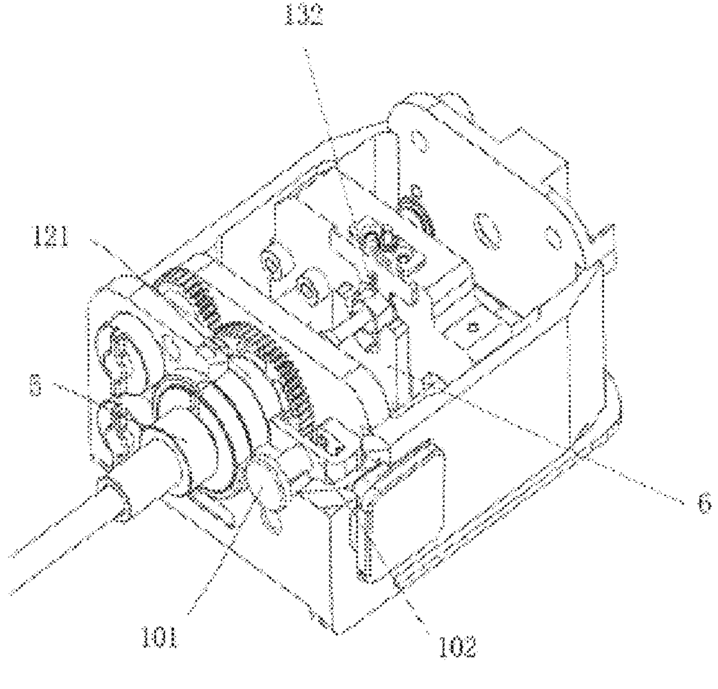
FIG. 5 is a view showing the power seat of the detachable manipulator device shown in FIG. 2, showing the locking mechanism.
Figure 6:
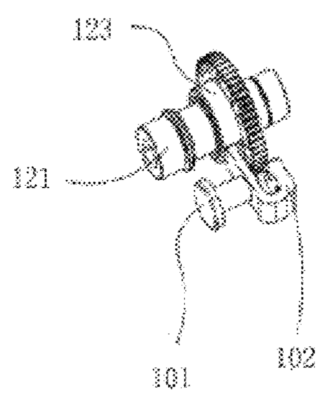
FIG. 6 is a perspective view showing the locking mechanism.

In the process of connecting the outer rod 21 of the instrument rod with the rotating shaft 121, when tightening the locking nut 5 on the distal end of the rotating shaft 121 or when detaching the instrument rod 2 from the rotating shaft 121, in order to facilitate tightening or loosening the locking nut 5, a locking mechanism 10 is provided. As shown in FIGS. 5 and 6, the locking mechanism 10 is provided on the distal end wall 14 of the housing 11, and includes a button 101, a pressing spring tab 102, and an elastic member (not shown) that biases the button 101 to an unlocked position. The pressing spring tab 102 includes a tooth 103 which can be engaged with and disengaged from the gear 123 provided on the periphery of the rotating shaft 3. Before tightening or loosening the locking nut 5, by pressing the button 101, the pressing spring tab 102 is pushed so that the teeth 103 thereof are meshed with the gears 123 of the rotating shaft 121, thereby preventing the rotating shaft 121 from rotating, so that the locking nut 5 can be tightened or loosened. After the locking nut 5 is tightened or loosened, the pressing spring tab 102 is biased to the position where the teeth 103 are separated from the gears 123 by means of the elastic member (not shown), so as not to hinder the rotation of the rotating shaft 123 during normal operation.

The inner rod 22 is extended inside the outer rod 21, through the rotating shaft 121, and to the sliding driving device 13. The inner rod 22 at its proximal end is formed with threads or fixed with a threaded connection 221. The threaded connection 221 is fixedly connected with the proximal end of the inner rod 22 by welding, bonding, press-fitting, etc., and the outer peripheral face thereof is formed with threads to connect with the threaded fixing shaft 132 of the sliding driving device 13. However, it should be noted that the present disclosure is not limited to threaded connection, and the proximal end of the inner rod 22 can also be connected with the sliding driving device by other detachable connection means, and the present disclosure is not limited thereto.

The sliding driving device 13 includes a slider 131, which is guided to slide in the axial direction. To drive the slider 131 to translate, a sliding drive mechanism (not labeled) is provided, which includes a sliding driving input joint 41 and a lead screw 42. As shown in FIG. 5, the sliding driving input joint 41 is provided on the end wall 14 and can be provided next to the rotary driving input joint 31 and is engaged by a sliding driver from a surgical robot. The slide driver is engaged with the slide driving input joint 41 and drives the lead screw 42 to rotate, and the slider 131 is threaded to the lead screw 42, thereby is slid along the axial direction with the rotation of the lead screw 42. Guide rails or guides (not shown) may be further provided in the housing 11 to guide the sliding movement of the slider 131.

A bearing 133 is arranged between the nut fixing shaft 132 and the slider 131, so that the nut fixing shaft 132 can rotate relative to the slider 4, but cannot move axially relative to the slider 131, thereby the nut fixing shaft 132 moves the inner rod 22 axially as the slider 131 moves; and is rotated together with the inner rod 22 as the outer rod 21 is driven by the rotary driving device.

In order to facilitate mounting or dismounting the end of the inner rod 22 or the threaded connection 221 with the nut fixing shaft 132, an anti-rotation mechanism is provided. The anti-rotation mechanism includes an engagement pressing tab 6 which is mounted on the distal side wall of the slider 4 by a spring 7 and can be operated from the outside of the housing 11 through an opening (not labeled) formed in the bottom wall of the housing 11. The engagement pressing tab 6 includes, for example, an engaging portion 61 formed with an opening 62 that can be engaged with the outer periphery of the threaded fixing shaft 132. As shown in the figures, the threaded fixing shaft 132 includes, for example, a hexagonal outer profile, whereby the opening 62 is formed in a shape similar to an opening of a wrench. However, this disclosure is not limited to this. For example, the outer periphery of the threaded fixing shaft 132 may be formed with anti-rotation structures such as teeth or other protrusions or recesses, and the corresponding end of the engagement pressing tab is formed with a shape to engage with the anti-rotation structures, thereby preventing the nut fixing shaft 132 from rotating during engagement.

The spring 7 biases the engagement pressing tab 6 in a direction in which the engagement pressing tab 6 is disengaged from the nut fixing shaft 132, thereby preventing the engagement pressing tab 6 from unintentionally engaging the nut fixing shaft 132 during operation. In order to more reliably prevent the engagement pressing tab 6 from engaging the nut fixing shaft 132 during the operation, the bottom surface of the housing 11 can also be provided with a stop block 9. The stop block 9 forms as a cantilever structure, which is, for example, extended within the operation range of the slider 4. As shown in FIG. 3, the engagement pressing tab 6 may further include a blocking portion 63. When the engagement pressing tab 6 moves with the slider 4 in its operation range, the blocking portion 63 of the engagement pressing tab 6 moves below the cantilever of the stop block 9, so that the engagement pressing tab 6 is prevented from being unintentionally pressed to engage with the nut fixing shaft 132 by the stop block 9.

Next, the disassembly and assembly operation of the instrument rod 2 according to the present disclosure as described above is briefly described.

When the instrument rod 2 is disassembled, it is firstly necessary to press the button 101 to cause the pressing elastic tab 102 catch the rotating gear 123, and then the locking nut 5 is rotated counterclockwise to be unscrewed, so that the instrument rod 2 can be driven with the driving slider 131 to move axially outward, that is, away from the instrument power seat. While moving outward, the blocking portion 63 of the engagement pressing tab 6 moves out of the blocking range of the stop block 9, so that the engagement pressing button 6 can be pressed down, causing the hexagonal opening 63 on the engagement pressing tab 6 engages with the external hexagonal stud on the threaded fixing shaft 132, then when further rotating the instrument rod 2 counterclockwise, the instrument rod 2 moves relative to the threaded fixing shaft 132, and finally, the inner rod 22 of the instrument rod 2 is disengaged from the driving slider 131, and then the instrument rod 2 can be pulled out and taken out, the instrument rod 2 is dismounted.

When the instrument rod 2 is to be installed, it is also necessary to press the button 101 firstly, then the outer rod 21 of the instrument rod 2 is inserted into the central hole of the rotating shaft 121 and the inner rod 22 is passed through the central hole of the rotating shaft 121, then the instrument rod 2 is rotated clockwise until the threaded connection 121 of the inner rod 21 is screwed with the nut fixing shaft 132, and then the driving slider 131 is pushed back to the normal position, so that the blocking portion 63 of the engagement pressing tab 6 is located under the cantilever of the stop block 9, finally, the locking nut 5 is installed and rotated clockwise to complete the installation of the instrument rod 2 on the instrument driving seat.

During the installation process, if the instrument rod 2 cannot be pulled out to move the driving slider 131, the engagement pressing tab 6 cannot be pressed. Thus, in order to enable the engagement pressing tab 6 to engage with the threaded fixing shaft 132, it is necessary to slide the slider 131. The end face of the instrument power seat is provided with a sliding driving input joint 41, which is connected with the lead screw 42 located inside the driving housing 11. The slider 131 is mounted on the lead screw 42, which can convert the rotary motion of the lead screw 42 into the linear motion of the slider 131. By manually screwing the input joint 41, the slider 131 can be driven to slide, so that the engagement pressing tab 6 is moved out of the stop block and can be pressed, and then the engagement pressing tab 6 can pressed to engage the hexagonal outer profile of the threaded fixing shaft, so that the threaded connection between the instrument rod 2 and the threaded fixing shaft 132 can be performed.

With the stop block 9 in the present invention, the engagement pressing tab 6 cannot be pressed during the normal operation, and only when the front locking nut 5 is removed and the instrument rod 2 is pulled out for a certain distance, can the instrument rod 2 be dismounted and mounted on the threaded fixing shaft 132, thus the normal and safe use of the instrument can be ensured.

In addition, because the engagement pressing tab 6 is connected with the return spring 7, the return spring 7 in the form of a compression spring can ensure that there is a gap between the engagement pressing tab 6 and the driving slider 131 when the engagement pressing tab 6 is not pressed, so that when the driving slider 131 is pushed inward, the stop block 9 can enter the gap, and the protection function of the stop block 9 during the normal operating conditions is enabled.

Next, referring to FIGS. 7 to 12, a detachable manipulator device according to another embodiment of the present disclosure is described. In the following description, the same or corresponding features are labeled by the same reference numerals, and the related descriptions thereof are omitted.

Figure 7:
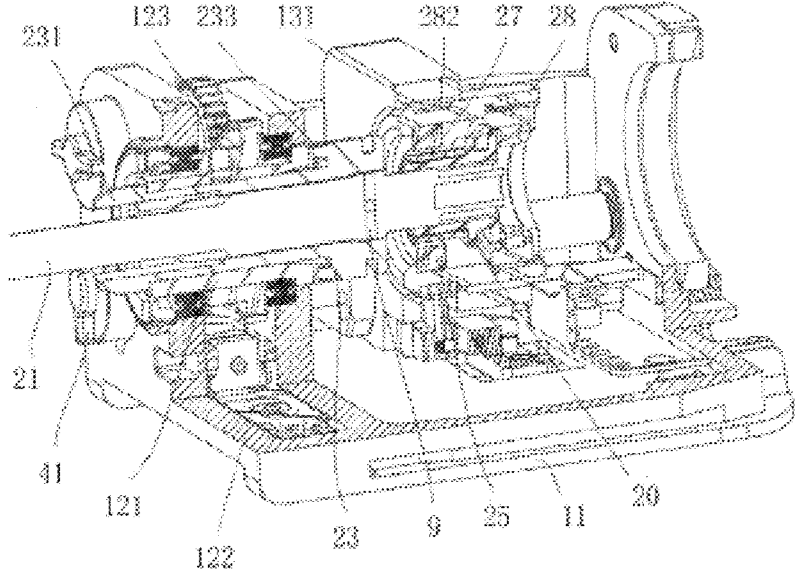
FIG. 7 is a cross-section view showing a power seat of a detachable manipulator device according to another embodiment of the present disclosure.
Figure 8:
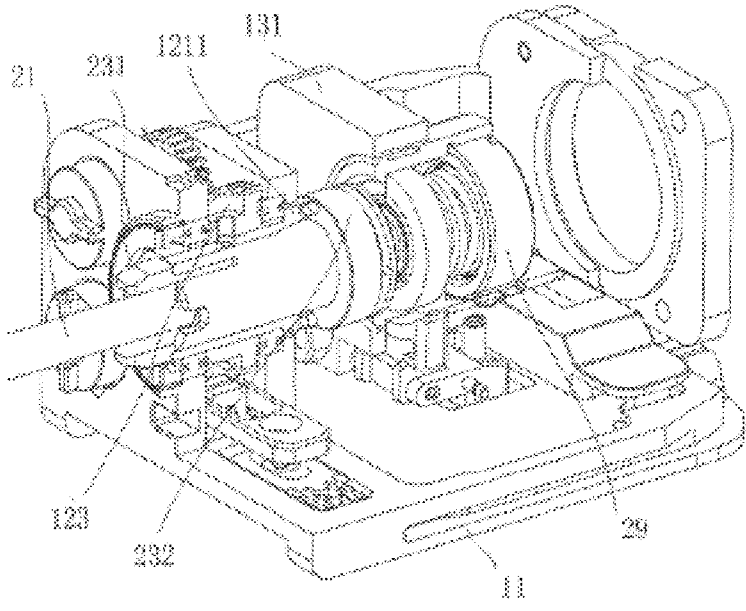
FIG. 8 is a cut-way view showing the detachable manipulator device shown in FIG. 7 from another angle.
Figure 9:
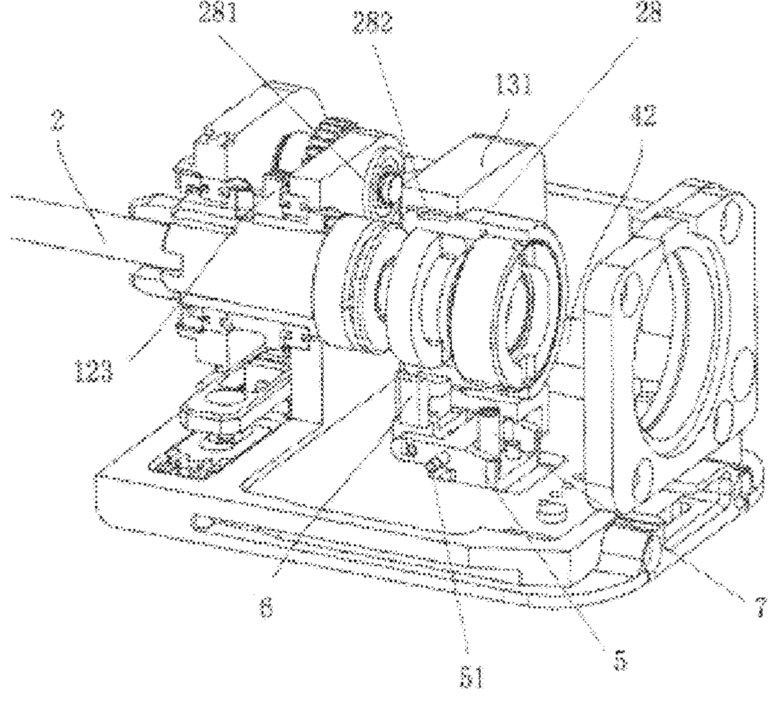
FIG. 9 is a cut-way view showing the detachable manipulator device shown in FIG. 7 from another angle.

As shown in FIG. 7, the instrument rod 2 is detachably connected to the power seat 1. Similar to the previously described embodiment, the power seat 1 includes a housing 11, in which a rotary driving device 12 and a sliding driving device 13 are provided. The rotary driving device 12 includes a rotating shaft 121 rotatably provided on two walls of the housing 11 through bearings 122, and a gear 123 is provided on the periphery of the rotating shaft 121 and meshes with the driving gear 32 of the rotating input device, thereby receiving the rotating input from the driver of the surgical robot.

The instrument rod 2 includes an outer rod 21 and an inner rod 22. The inner rod 22 can move axially in the outer rod 21, but the outer rod 21 and the inner rod 22 can only rotate together.

A rotary fixing member 23 is fixedly provided on the outer periphery of the outer rod 21, the rotary fixing member 23 is fixed on the outer periphery of the outer rod 21 by various means such as splines, pins, bonding, welding, etc. The rotary fixing member 23 is provided with an inverted hook 231 at its distal end, a flange 232 extending radially outward at its proximal end, and at least one protruding boss 233 at the end face (distal end face) of the flange 232 facing the rotating shaft 121. In the illustrated embodiment, the rotary fixing member 23 is fixedly connected to the outer rod 21 by the pin 9.

Referring to FIGS. 7-12, the front end of the rotary fixing member 23 is connected with an inverted hook 231, and the outer diameter of the segment on the outer rod 21 corresponding to the inverted hook 231 is smaller than the inner diameter of the central hole of the rotating shaft 121 through which the outer rod 21 passes. During installation, the inverted hook 231 extended from the proximal end of the rotating shaft 121 is inserted into the central hole of the rotating shaft 121 by deforming inwardly and passed out from the front end of the rotating shaft 121, so that the claws of the inverted hook 231 are snap-fitted and connected to the front-end face of the rotating shaft 121, thereby preventing the rotation fixing member 23 from moving back and forth in the axial direction.

The end face of the flange 232 of the rotary fixing member 23 on which the protruding boss 233 is provided abuts against the rear end face (proximal end face) of the rotating shaft 121, and the inner end of the rotary fixing member 23 is provided with a flange which can be fitted and fixed to the inner end face of the rotating shaft 121. And the flange and the rotating shaft 121 are connected through a concave-convex connecting portion. For doing so, at least one groove 1211 is formed in the proximal end face of the rotating shaft 121. When the distal end face of the flange 232 of the rotary fixing member 23 abuts against the proximal end face of the rotating shaft 121, the protruding boss 233 of the rotary fixing member 23 is inserted into the groove 1211 of the rotating shaft 121, thereby enabling the rotary fixing member 23 to rotate together with the rotating shaft 121.

In this embodiment, a cylindrical groove 1211 is peripherally arranged on the rear end face of the rotating shaft 121, and the grooves 1211 are provided on the proximal end face of the rotating shaft 121 regularly. The protruding bosses 233 are arranged on the front-end face (distal end face) of the rotary fixing member 23. In this embodiment, two symmetrical protruding bosses are arranged on the front end face of the rotary fixing member 23 in order to enable the protruding bosses 233 to be inserted into the groove 1211 more easily and quickly. After the two protruding bosses 233 are completely inserted into the groove 1211, the inverted hook 231 at the front end of the rotary fixing member 23 snaps onto the front-end face of the rotating shaft 121 to ensure that the outer rod 21 is completely fixed in the axial direction. The number of the protruding bosses 233 shall be able to ensure that they can be smoothly guided and inserted into the grooves 1211 on the end face of the rotating shaft, shall not be limited to odd and even numbers, and meet the requirements of uniform arrangement.

In order to guide the protruding boss 233 into the groove 1211 in the rotating shaft 121 and ensure the smooth installation process of the instrument rod 2, the top end of the protruding boss 233 can be chamfered. With this arrangement, the rotating part of the instrument rod 2 can be more quickly fitted and connected with the rotating shaft 121, thus realizing the rapid installation of the instrument rod 2.

Figure 10:
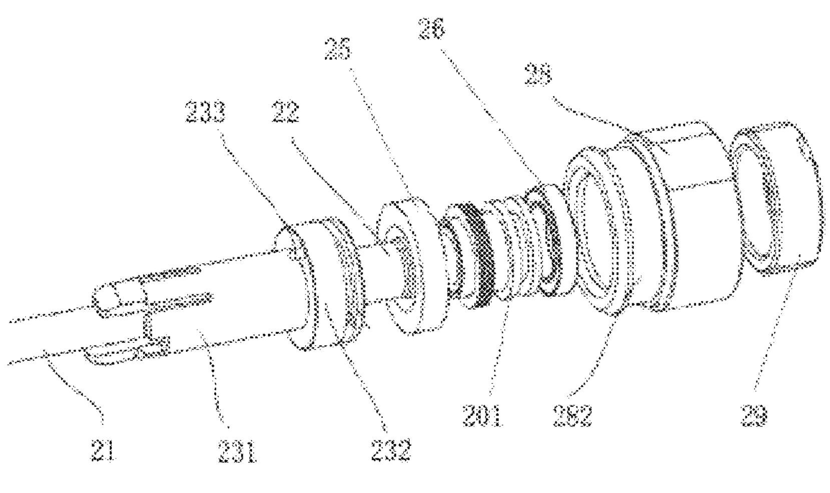
FIG. 10 is an exploded view showing the part where the inner rod and the slider are engaged.
Figures 11, 12:
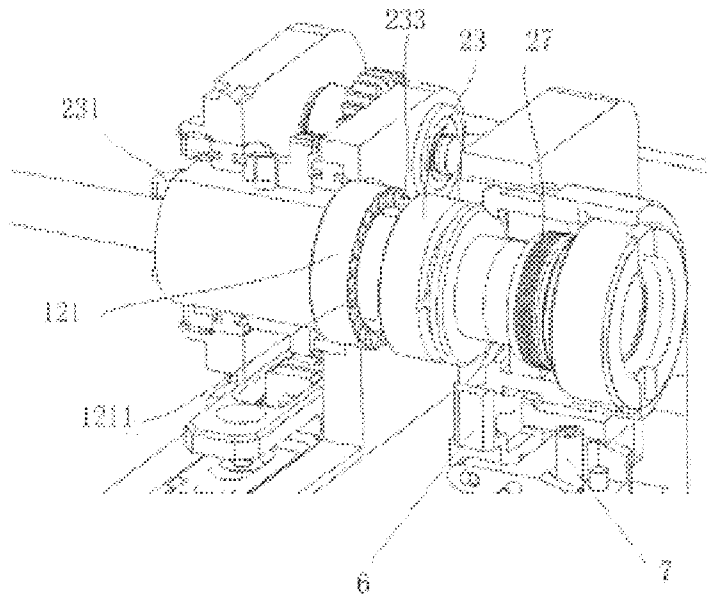
FIG. 11 is a schematic view showing the state before an inner rod is engaged with a slider.
FIG. 12 is a schematic view showing the state after the inner rod is engaged with the slider.

Referring to FIGS. 10 to 12, the detachable installation of the instrument rod 2 and the sliding driving device 13 will be described. The sliding driving device 13 includes a slider 131 which receives the rotation input from the sliding driving input joint 41 through a lead screw 42, thereby is driven to slide in the housing 11. The slider 131 includes a central hole 134, and the proximal part of the inner rod 21 is rotatably but not axially movably engaged in the central hole of the slider 131, so that the inner rod 21 can slide with the slider 131.

Referring to FIGS. 10 to 12, FIG. 10 shows an exploded view of the part where the inner rod 21 is engaged with the slider 131, FIG. 11 shows a view of the state before the inner rod 21 is engaged with the slider 131, and FIG. 12 is a view after the inner rod 21 is engaged with the slider 131. A snap-fitting member 20 is fixedly arranged at the proximal end of the inner rod 21, and the snap-fitting member 20 is provided with an annular flange 201, preferably two annular flanges 201, in the axial direction.

A locking ring member 28 is provided on the periphery of the proximal end of the inner rod 21, and the inner rod 21 is detachably connected to the central hole of the slider 131 through the locking ring member 28.

The distal end of the locking ring member 28 is provided with a flange 281 protruding radially inward, and the inner peripheral face of the proximal end of the locking ring member 28 is provided with an internal thread (not labeled). The outer periphery of the inner rod 21 is fixed with a bearing 25, which is inserted into the central hole of the locking ring member 28, and the distal end face of the bearing 25 abuts against the flange 281, facing the proximal side along the axial direction of the inner rod 21. The outer periphery of the inner rod 21 is also provided with a spring 27, which is compressed between the bearing 25 and the annular flange 201, thereby providing a certain degree of axial flexibility for the inner rod 21.

The locking plug 29 is screwed into the proximal end of the locking ring member 28, and a bearing 26 is provided between the locking plug 29 and the flange 201, and the flange 201 abuts against the bearing 26 in the axial direction. Therefore, the bearing 25, the spring 27, the inner rod and the snap-fitting member 20, and the bearing 26 are assembled together by means of the flange 218 at the distal end of the locking ring member 28 and the locking plug 29 screwed into the proximal end to form a subassembly. And with the bearings 25 and 26, the inner rod 22 can rotate relative to the locking ring member 28 but cannot move axially relative to the locking ring member 28. In addition to the threaded connection, the locking plug 29 can also be connected to the locking ring member 28 by other means such as snap connection and so on. For example, as shown in FIG. 12, a groove 291 is formed on the proximal end of the locking plug 29, and a protrusion 284 is formed on the inner peripheral face of the proximal end of the locking ring member 28, thereby snapping the locking plug 29 into the proximal end of the locking ring member 28.

As shown in FIG. 12, an annular snap-fitting groove 282 is formed on the outer peripheral face of the locking ring member 28 to cooperate with the slider 121. A locking tongue 6 is provided on the side wall of the central hole 124 of the slider 121, and the locking tongue 6 penetrates into the central hole 124, so that it can be engaged with the annular snap-fitting groove 282 on the peripheral face of the locking ring member 28, thereby the locking ring member 28 and the slider 121 can move along the axial direction together. The lower side of the locking tongue 6 is provided with a locking button 5, which is arranged in the side wall of the slider 121 in the form of a lever, for example, and exposed to the outside of the housing 11 through an opening (not labeled) of the housing 11, so as to operate the locking button 5 from the outside of the housing 11. The locking button 5 is arranged in the side wall of the slider 121 through the pivot 51, whereby pressing the locking button 5 will pull the locking tongue 6 away from the groove 282, so that the locking tongue 6 is disengaged from the snap-fitting groove 282. The locking button 5 is also provided with a spring 7, which biases the locking button 5 outward, thereby biasing the locking tongue 6 toward the center hole, that is, toward the engagement position with the snap-fitting groove 282 of the locking ring member, through the leverage function of the locking button 5.

Therefore, when the instrument rod 2 including the locking ring member 28 is inserted into the central hole 124 of the slider 121 from the rear side (the proximal side), the locking tongue 6 is snap-fitted into snap-fitting groove 282 by adjusting the axial position of the slider 124, so that the instrument rod 2 is engaged with the slider 121.

The detachable operation process of the instrument rod 2 according to this embodiment will be described below:

When the surgical instrument needs to be disassembled after use, it is necessary to disassemble the disposable instrument rod 2. First, press the locking button 5 on the power seat 1 to control the expansion and contraction of the locking tongue 6, and at the same time press the two inverted hooks 231 at the front end of the rotating shaft 121, so that the inverted hooks 231 can be elastically retracted into the rotating shaft 121, and then push the instrument rod 2 to the rear of the power seat 1, so that the instrument rod 2 can be conveniently taken out.

Referring to FIGS. 10 to 12, when the instrument rod 2 needs to be installed, the instrument rod 2 is inserted from the rear side, that is, the proximal side, of the power seat 1. After the two inverted hooks 231 of the rotary fixing member 23 on the instrument rod 2 are caught on the front end face of the rotating shaft 121, the sliding driving input joint 41 on the power seat 1 is rotated counterclockwise by hand, so that the slider 131 is passively moved and the locking tongue 6 is fitted with the snap-fitting groove 282 until the sound of "click" is heard, it indicates that the locking tongue 6 has been caught into the snap-fitting groove 282 of the locking ring member 28 of the instrument rod 2 to complete the installation of the instrument rod 2.

When the surgical manipulator according to the present disclosure is using in the surgical operation, the rotation action of the outer rod 21 of the instrument rod 2 is controlled by the rotating shaft 121, and the movement of the inner rod 22 of the instrument rod 2 is controlled by the slider 131, so that the forward, backward and opening and closing operations of the surgical instruments installed at the distal end can be controlled.

The outer rod 21 is connected with the rotary fixing member 23 by a pin shaft 29, and the snap-fitting member 20 fixedly connected with the inner rod 22 is installed in the locking ring member 28. The locking ring member 28 is also provided with a spring 27 and a bearing 26 connected thereto for controlling the forward and backward movement of the snap-fitting member 20, so that the inner rod 22 and the snap-fitting member 20 can rotate in the locking ring member 28 following the rotating shaft 121. The snap-fitting member 20, the inner rod 22, the outer rod 21, the rotary fixing member 25 and the locking ring member 28 are preferably pre-assembled as a sub-assembly. When replacing, the whole sub-assembly is replaced to reduce the risk of cross-contamination.

The above description of the disclosed embodiments enables those skilled in the art to implement or use the invention. Many modifications to these embodiments will be obvious to those skilled in the art, and the general principles defined herein can be implemented in other embodiments without departing from the spirit or scope of the present invention. Therefore, the present invention will not be limited to the embodiments shown herein but will be conformed to the widest scope consistent with the principles and novel features disclosed herein.

We claim:

1. A detachable manipulator device comprising a power seat, an instrument rod extending from the power seat, and an end effector arranged at a distal end of the instrument rod, wherein the instrument rod is detachably mounted on the power seat to transmit rotary motion and sliding motion from the power seat to the end effector, wherein the instrument rod comprises an outer rod and an inner rod, and the inner rod is arranged within the outer rod so as to be axially movable relative to the outer rod and non-rotatable relative to the outer rod.

2. The detachable manipulator device according to claim 1, wherein the power seat comprises a housing, a rotary driving device provided in the housing, and a sliding driving device provided in the housing, and wherein the rotary driving device drives the outer rod and the inner rod to rotate, and the sliding driving device drives the inner rod to slide in the axial direction.

3. The detachable manipulator device according to claim 2, wherein the rotary driving device drives a rotating shaft, wherein the outer rod is detachably engaged with the rotating shaft to rotate together with the rotating shaft, and wherein the outer rod is axially fixed relative to the rotating shaft.

4. The detachable manipulator device according to claim 3, wherein the outer rod comprises a flat shaft segment with a non-circular cross section, wherein the rotating shaft comprises a central hole with a corresponding cross section, and wherein the flat shaft segment of the outer rod is inserted into the central hole.

5. The detachable manipulator device according to claim 4, wherein the outer rod is further provided with a positioning flange and a locking nut, wherein the locking nut is threaded with a distal end of the rotating shaft to sandwich the positioning flange of the outer rod between the locking nut and the rotating shaft, so that the outer rod and the rotating shaft are axially fixed.

6. The detachable manipulator device according to claim 5, wherein an outer peripheral face of the rotating shaft is provided with a gear to receive rotational input, and wherein the housing is provided with a locking mechanism which is selectively engaged with the gear to selectively prevent the rotating shaft from being rotated.

7. The detachable manipulator device according to claim 6, wherein the locking mechanism comprises a button, a pressing spring tab driven by the button to engage with the gear, and an elastic member biasing the button towards a state that the pressing spring tab is disengaged from the gear.

8. The detachable manipulator device according to claim 4, wherein the outer rod of the instrument rod is fixedly connected with a rotary fixing member, wherein a distal end of the rotary fixing member includes an elastically deflectable inverted hook and a proximal end of the rotary fixing member includes a flange, wherein the rotary fixing member is inserted into the central hole of the rotating shaft such that the inverted hook is snap-fitted on a distal end face of the rotating shaft, and the flange abuts against a proximal end face of the rotating shaft.

9. The detachable manipulator device according to claim 8, wherein at least one protruding boss is formed on an end face of the flange of the rotary fixing member facing the proximal end face of the rotating shaft, wherein at least one groove is formed on the proximal end face of the rotating shaft, and wherein the at least one protruding boss is selectively fittable into the at least one groove.

10. The detachable manipulator device according to claim 9, wherein the outer rod is connected with the rotary fixing member by a pin.

11. The detachable manipulator device according to claim 2, wherein the sliding driving device comprises a slider, and wherein the inner rod is threaded with the slider.

12. The detachable manipulator device according to claim 11, wherein a proximal end of the inner rod is provided with threads, wherein the slider is provided with a rotatable threaded fixing shaft, wherein the rotatable threaded fixing shaft is axially fixed relative to the slider, and wherein the threads of the inner rod are threadedly engaged with the threaded fixing shaft.

13. The detachable manipulator device according to claim 12, wherein the slider includes an anti-rotation mechanism, wherein the anti-rotation mechanism selectively prevents rotation of the threaded fixing shaft.

14. The detachable manipulator device according to claim 13, wherein the anti-rotation mechanism includes an engagement pressing tab operable from the outside of the housing, wherein the engagement pressing tab is capable of engaging the outer periphery of the threaded fixing shaft to selectively prevent the threaded fixing shaft from rotating, wherein the engagement pressing tab is selectively movable between a locking position wherein the engagement pressing tab is engaged with the threaded fixing shaft and a disengaged position wherein the engagement pressing tab is disengaged from the threaded fixing shaft, and wherein the anti-rotation mechanism further comprises a spring biasing the engagement pressing tab toward the disengaged position.

15. The detachable manipulator device according to claim 14, wherein an inside of the housing is further provided with a stop block, wherein the stop block prevents the engagement pressing tab from being placed in the locking position.

16. The detachable manipulator device according to claim 2, wherein the sliding driving device comprises a slider including a central hole, and wherein a proximal end of the inner rod is provided with a locking ring member which is detachably fitted in the central hole of the slider.

17. The detachable manipulator device according to claim 16, wherein an outer peripheral face of the locking ring member includes a snap-fitting groove, and a side wall of the slider is provided with a locking tongue which can be moved between a locking position engaged in the snap-fitting groove and a disengaged position disengaged from the snap-fitting groove.

18. The detachable manipulator device according to claim 17, further comprising a spring that biases the locking tongue toward the locking position.

19. The detachable manipulator device according to claim 18, further comprising a locking button provided on the side wall of the slider, wherein the locking button can be actuated from outside of the housing to drive the locking tongue toward the disengaged position, wherein the locking ring member comprises a central hole, wherein the inner rod is rotatable arranged in the central hole, and wherein the inner rod is axially immovably arranged in the central hole of the locking member.

* * * * *